United States Patent [19]

Early et al.

[11] Patent Number: 4,468,428

[45] Date of Patent: Aug. 28, 1984

[54] HYDROPHILIC MICROFIBROUS ABSORBENT WEBS

[75] Inventors: Allen D. Early, Cincinnati, Ohio; David W. Cawlfield, Cleveland, Tenn.; Trevor Walker, Cincinnati; Paul T. Weisman, Fairfield, both of Ohio

[73] Assignee: The Procter & Gamble Company, Cincinnati, Ohio

[21] Appl. No.: 383,686

[22] Filed: Jun. 1, 1982

[51] Int. Cl.$^3$ .............................................. D02G 3/00
[52] U.S. Cl. ................... 428/221; 427/397.7; 427/430.1; 428/375; 428/393; 428/401; 428/452; 428/903; 428/913
[58] Field of Search ............... 428/903, 913, 221, 375, 428/393, 401, 452; 427/397.7, 430.1

[56] References Cited

U.S. PATENT DOCUMENTS

| | | | |
|---|---|---|---|
| 2,443,512 | 6/1948 | Powers et al. | 19/66 R |
| 4,041,203 | 8/1977 | Brock et al. | 428/903 |
| 4,049,764 | 9/1977 | Sigl et al. | 264/178 F |
| 4,093,765 | 6/1978 | Schmidt | 428/134 |
| 4,100,324 | 6/1978 | Anderson et al. | 428/288 |
| 4,196,245 | 4/1980 | Kitson et al. | 428/903 |
| 4,219,024 | 8/1980 | Patience et al. | 604/366 |
| 4,233,345 | 11/1980 | Elias et al. | 427/325 |
| 4,307,143 | 12/1981 | Meitner | 252/91 |
| 4,307,721 | 12/1981 | Tsuchiya et al. | 604/370 |

FOREIGN PATENT DOCUMENTS 2066145 7/1981 United Kingdom.

Primary Examiner—William J. Van Balen
Attorney, Agent, or Firm—Jacobus C. Rasser; Steven J. Goldstein; Jack D. Schaeffer

[57] ABSTRACT

Fibrous absorbent webs having a low density (about 0.01 g/cm$^3$ to about 0.15 g/cm$^3$) and comprising at least about 50% hydrophilic microfibers, such as cellulose microfibers, having a diameter of from about 0.01 microns to about 15 microns possess superior absorption properties, especially under typical usage conditions.

Hydrophobic microfibers may also be used, provided such fibers are hydrophilized before or after web formation.

24 Claims, No Drawings

HYDROPHILIC MICROFIBROUS ABSORBENT WEBS

TECHNICAL FIELD

This invention relates to highly absorbent fibrous webs and methods for making them.

More specifically, the absorbent webs of this invention are characterized by their relatively low density and content of hydrophilic fiber having a relatively small diameter.

Disposable absorbent structures like diapers, towel sheets, napkins, surgical sponges, and the like, generally comprise an absorbent fibrous web. Such webs generally consist of cellulose fibers having a diameter of about 30 microns, randomly arranged in the web. This random arrangement is obtained by wet laying, air laying or solvent laying of the fibers. In the wet laying process the fibers are slurried in water; the water is subsequently drawn off and the web is dried. Solvent laying is similar to wet-laying, but an organic solvent is used instead of water. Air laying involves "slurrying" of dry fibers in an air stream and formation of a web by gravity and hydraulic forces. Wet cellulose fibers are soft and pliable. This causes fibers in a wet web to sag against each other and the web structure to collapse to a certain extent. During subsequent drying the web collapses even more due to surface tension forces. Solvent-laid webs and particularly air-laid webs suffer much less structural collapse. Such webs therefore generally have a lower density than wet-laid webs. A lower density web has a greater potential absorbent capacity.

On the other hand, in webs formed by air-laying or solvent-laying there is little, if any, of the hydrogen bonding among the fibers which develops when wet cellulose fibers are dried in contact with each other. Air-laid and solvent-laid webs therefore have poor dry strength and wet strength characteristics. Wet strength additives which are generally employed to improve the mechanical strength of such webs tend to reduce the hydrophilicity of the web.

Other methods used to improve the strength of an absorbent web include mixing the web with hydrophobic thermoplastic fibers. Such fibers can be bonded by heat fusion to form a high strength matrix for the intermixed hydrophilic fibers. Small diameter hydrophobic thermoplastic fibers have been reported to "bind" each other and the hydrophilic fibers by entanglement, thus obviating the necessity of heat fusion. Although mixing of thermoplastic fibers with hydrophilic fibers effectively increases the strength of an absorbent web, the hydrophobicity of such fibers adversely affects the absorption capacity and the wicking properties of the web.

It has been suggested to improve the wettability of hydrophobic fibers by impregnating such fibers with a surfactant. This treatment of the fibers does improve their wettability, but the mechanism through which this is achieved (i.e., lowering of the surface tension of the water) reduces the capability of absorbent webs to remove aqueous liquids from surfaces (e.g., coffee from a table top, urine from skin, etc.). There is, therefore, a need of a method to hydrophilize hydrophobic thermoplastic fibers without lowering the surface tension of the fluid to be absorbed.

The practical usefulness of an absorbent web is determined not so much by its potential absorption capacity, but rather by the fraction thereof which partitions water under normal usage conditions (e.g. water spill wipe-up in the case of a disposable towel sheet), the "useful capacity" of the absorbent web. Typically, the useful capacity of a cellulose fiber web is in the order of 25% (or less) of the potential absorption capacity. Attempts to increase the useful capacity of absorbent webs so far have not been successful, or have resulted in an unacceptable reduction of the wicking properties of such webs, that is the rate at which the webs take up water.

It is therefore an object of this invention to provide an absorbent web which has superior absorbency, under typical use conditions, high wicking rates and good wet strength properties. Another object of this invention is to improve the wet strength of absorbent webs without reducing their wicking properties. It is also an object of this invention to provide processes by which the superior absorbent webs of this invention can be made.

BACKGROUND ART

Numerous attempts to improve the wicking properties and wet strength properties of highly absorbent web structures have been described in the art.

Sigl, et al., U.S. Pat. No. 4,049,764, issued Sept. 20, 1977, disclose an extrusion process for the formation of cellulose fiber webs. Highly absorbent and rapidly wicking filaments and web structures are formed when the extrudate is treated prior to extrusion with a solvent like acetone.

Schmidt, U.S. Pat. No. 4,093,765 issued June 6, 1978, deals with a method of increasing the wet strength of a wet-laid wood pulp fiber web. After drying of the web wet strength additives like urea formaldehyde or melamine formaldehyde are applied to the surface of the web only, to minimize the loss of absorption capacity. In a similar way, Elias, et al., (U.S. Pat. No. 4,233,345 issued Nov. 11, 1980) improved the wet strength of an air laid cellulosic fiber web by lightly spraying with a solution of a coagulating material, e.g. Carbopol 940 after the web is formed.

Tsuchiya, et al., U.S. Pat. No. 4,216,772 issued Aug. 12, 1980, achieved improved structural integrity of a non-woven absorbent structure by admixing therein from 10 to 40% of a hydrophobic thermoplastic fiber and subsequent heat fusion of these fibers. A similar approach was taken by Patience, et al., U.S. Pat. No. 4,219,024 issued Aug. 26, 1980, who provide wet strength properties to an absorbent pad by admixing particles of plastic material which are fused to the fibers in the pad.

U.S. Pat. No. 4,100,324, issued July 11, 1978 to Anderson, et al., discloses the use of hydrophobic thermoplastic fibers of small diameter to increase the strength of cellulose fiber absorbent webs. The thin fibers keep the cellulose fibers together by mechanical entanglement, thus obviating the need of heat fusion.

The common feature of the last five of the cited patents is that they describe an attempt to improve wet strength properties of an absorbent structure by limited application of a relatively hydrophobic wet strength additive. Although loss of absorbency and wicking rates may be minimized by such limited application, the use of hydrophobic materials in absorbent webs to achieve requisite structural integrity inevitably leads to a loss of hydrophilic properties.

SUMMARY OF THE INVENTION

The present invention is a fibrous absorbent web comprising at least about 50% of hydrophilic microfibers having a diameter of from about 0.01 microns to about 15 microns, said web having a density of from about 0.01 g/cm$^3$ to about 0.15 g/cm$^3$. The absorbent webs of this invention posses a high useful absorption capacity under typical usage conditions rendering them suitable for use in various products such as diapers, towel sheets, surgical sponges, tampons, and the like. These high useful absorption capacities are achieved without loss of wicking properties or structural integrity.

Both hydrophilic and hydrophobic fibers can be used in the absorbent webs of the present invention, but hydrophobic fibers must subsequently be hydrophilized. Hydrophobic fibers may be hydrophilized after formation of the web by coating the fibers with a hydrophilic material. Any hydrophilic material which has substantivity to the fibers is suitable for this purpose. If necessary, binding of the web is achieved without loss of absorption capacity or wicking rates by adsorption of a cellulose ester e.g., cellulose acetate, and subsequent hydrolysis of the ester. Treatment of a web with colloidal silica results in both binding and hydrophilizing of the web.

A process for making the absorbent web is also part of this invention.

DETAILED DESCRIPTION OF THE INVENTION

Definitions of terms used herein are as follows.

By "microfiber" herein is meant a fiber having a diameter of about 15 microns or less.

By "hydrophilic (micro)fiber" herein is meant a (micro)fiber which is hydrophilic by nature (as, e.g., cellulose) or a (micro)fiber which is hydrophilic by virtue of chemical modification of the surface or a substantive coating on the surface of the (micro)fiber.

By "%" and "percentage" herein is meant weight % and weight percentage, respectively, unless otherwise indicated.

By "actual capacity" herein is meant the amount of liquid (in ml) absorbed by 1 g of absorbent web under soaking conditions.

By "useful capacity" herein is meant the amount of liquid (in ml) absorbed by 1 g of absorbent web under representative usage conditions (e.g. spill wipe-up).

"Wicking" as used herein refers to the propensity of an absorbent web to be wetted by the liquid to be absorbed; similarly, "wicking rate" denotes the rate at which an absorbent web is wetted by the liquid to be absorbed.

The "specific surface area" as used herein is the total surface area (in m$^2$) of the fibers of 1 g of a web that is accessible to molecules of the liquid to be absorbed, as estimated by nitrogen adsorption at a temperature of 78 K.

The absorbent webs of this invention are comprised of fibers at least 50% of which are hydrophilic microfibers having a diameter of from about 0.01 micron to about 15 microns. Preferably at least 80% of the fibers are hydrophilic microfibers having a diameter of from about 0.01 micron to about 15 microns. The webs have a density of from about 0.01 g/cm$^3$ to about 0.15 g/cm$^3$. The density determines the maximum potential water uptake capacity. The practical utility of an absorbent web is to a high degree determined by the amount of water that can be taken up at negative hydrostatic pressures. It has been found that the water absorption capacity at a hydrostatic pressure of $-25$ cm water correlates well with the utility of the absorbent web in the wipe up of water spills. The water absorption capacity at $-25$ cm H$_2$O correlates well with the useful capacity defined above. The useful capacity is used throughout this application for characterization of absorbent webs.

It has been found that low density (from about 0.01 g/cm$^3$ to about 0.15 g/cm$^3$) webs which are made of fibrous hydrophilic material comprising at least about 50% fibers having a diameter in the range of from about 0.01 microns to about 15 microns, posses a surprisingly high useful capacity. Due to this high useful capacity the absorbent webs of this invention absorb two to four times more water than conventional absorbent webs under typical usage conditions (e.g. spill wipe-up).

The use of large quantities of microfibers inevitably results in an increase of the specific surface area of the web. The generally accepted physical model for wicking through cylindrical capillaries, as is used as the basis for the Lucas-Washburn equation, predicts the wicking rate to decrease with increasing specific surface area. Yet, the webs of this invention possess wicking rates which compare favorably with those of conventional webs.

The basic advantage of the webs of the present invention over conventional webs is that a high percentage of the actual capacity is available as useful capacity. The actual capacity itself is largely determined by the density of the web: generally speaking, the lower the density, the higher the actual capacity. The absorption benefits obtained with fibrous webs comprised of at least 50% microfibers can only be fully exploited when the webs are of relatively low density, i.e., less than about 0.15 g/cm$^3$. Webs of extremely low density have insufficient integrity for practical use; therefore, the density of the microfibrous webs should be at least about 0.01 g/cm$^3$. Preferred for use herein are webs which have a density of from about 0.04 g/cm$^3$ to about 0.10 g/cm$^3$.

The superior absorption characteristics which are typical for the webs of the present invention are obtained when at least about 50% of the fibers in the web are hydrophilic microfibers. The length of these microfibers is not critical and may range from less than 0.1 mm to several centimeters or more. Preferred for use herein are microfibers which have a diameter of from about 0.5 microns to about 10 microns. Preferred absorbent webs comprise at least about 80% microfibers. Webs consisting essentially completely of microfibers are most highly preferred.

The webs may include up to about 50% of fibers which are not microfibers, i.e. which have a diameter of appreciably more than 15 microns. Such fibers may be of the same or different composition as the microfibers, and of similar or different length. Examples are wood pulp fibers, which have a diameter of about 30 microns, nylon fibers as used in the textile industry (in the order of 50 microns diameter) and the like. The nature of these fibers is not critical to the present invention. Their selection may be based on factors like strength, availability and cost, and can routinely be made by a person skilled in the art.

Any fiber can be used as microfibers in the absorbent webs of this invention given appropriate diameter. Hence, fibers may be hydrophilic or hydrophobic. Hyhydrophobic fibers, of course, have to be hydrophilized before or after manufacture of the web to make them suitable for applications requiring absorption of water. Hydrophilic fibers may be inorganic, like alumina or aluminum, or organic like cellulose or rayon. Hydrophilic fibers do not require a separate hydrophilization process and are therefore preferred for use herein. Cellulose fibers are abundantly available at low cost and are therefore preferred hydrophilic fibers for use herein.

The fiber diameter can be determined by means of scanning electron microscopy (SEM). SEM photophgraphs of fiber samples are used to determine the mean fiber diameter and the fiber diameter distribution. The percentage of microfibers present in a sample as determined by this technique is a number percentage. This can be converted to an approximate weight percentage using standard statistical techniques.

The most common source of cellulose fibers, wood pulp, contains fibers having a diameter of about 30 microns. These fibers can be fibrillated to microfibers having a diameter of about 10 microns by subjecting an aqueous suspension to high shear forces. Beaters as used in the papermaking industry are suitable provided the wood pulp has a consistency of from about 5% to about 6% and a beater roll pressure of about 100 lbs. to about 200 lbs. (about 90 kg to about 180 kg). Fibers of the required diameter are obtained after processing the beater for about 60 minutes to about 120 minutes. An example of a suitable beater is the type known in the paper industry as the hollander beater. A more detailed description of beaters and their operation is found in Kirk-Othmer, *Encyclopedia of Chemical Technology*, 2nd ed. Vol. 14 (Wiley-Interscience 1967) pp 497-500, incorporated herein by reference. Such high shear forces may also be realized in a colloid mill or in a homogenizer. Particularly suitable are the homogenizers which are being widely used in the food and cosmetics industry and referred to as Gaulin or Maton-Gaulin homogenizers.

Cellulose fibers of the required thickness may also be obtained directly from natural sources like abaca and cereal straws (e.g., wheat or rice). The natural fibers as they are obtained from the plant are in the form of a so-called drylap. In this drylap the fibers are entangled in each other in conglomerates with a diameter of several tens of microns. To obtain single fibers therefrom the drylap is subjected to a moderate shear action as occurs in the carding of wool. Such shear forces are also present in a hammer mill type disintegrator. Commercially available abaca is classified according to fiber diameter. The class which has a natural fiber thickness of from about 10 microns to about 15 microns is preferred for this embodiment of the invention.

Microfibers of cellulose may also be obtained by spinning a solution of cellulose in a suitable solvent, and subsequently stretching the yarn to the required diameter. Cellulose may also be solubilized by converting it to e.g. nitrocellulose, cellulose xantham, or cuprammonium cellulose. The latter two may be regenerated to cellulose after spinning. The techniques of derivatizing cellulose are known in the textile fiber art and are described in B. P. Corbman, "Textiles: Fiber to Fabric", fifth edition, 1975, McGraw-Hill, New York, in Chapter 15. Other examples of soluble cellulose derivatives are cellulose acetate and cellulose triacetate (see Corbman, supra, Chapter 16).

Once cellulose fibers of the required thickness have been obtained, the absorbent web may be formed therefrom by conventional techniques like wet-laying, air-laying or solvent-laying. These techniques are well known in the art. Wet-laying involves slurrying the fibers in water and depositing the mass of randomly oriented fibers on a wire screen. This technique is described in more detail in U.S. Pat. No. 4,093,765, issued June 6, 1978, to Schmidt, which disclosure is incorporated herein by reference. Solvent laying is a similar technique using a non-aqueous solvent instead of water. The fibers may initially be slurried in water and the water subsequently be replaced with another solvent. This technique is described in U.S. Pat. No. 3,826,711, issued July 30, 1974 to Schoggen, et al., the disclosure of which is incorporated herein by reference. The technique of air-laying uses air as slurrying medium for the fibers. A more detailed description of this technique is found in U.S. Pat. No. 4,129,132, issued Dec. 12, 1978, to Butterworth, et al., incorporated herein by reference. Webs having a density of less than 0.15 g/cm$^3$ are more readily obtained by air-laying or solvent-laying. These techniques are therefore preferred for use herein.

The cellulose microfiber web may be used as the absorbent core of a disposable diaper or an absorbent bandage. Disposable diapers are well known in the art and disclosed in, e.g., U.S. Pat. No. 3,794,038, issued Feb. 26, 1974 to Buell, and in U.S. Pat. No. 3,952,745, issued Apr. 27, 1976 to Duncan, both of which are incorporated herein by reference. The conventional diapers disclosed in these references comprise an air-laid web of wood pulp fibers as an absorbent pad. When the conventional absorbent pad is replaced with an absorbent web of the present invention, a diaper is obtained which has superior liquid containment and rewet properties.

Like disposable diapers, disposable sanitary napkins comprise an absorbent pad which is generally an air-laid wood pulp fiber web. Examples of such napkins are disclosed in U.S. Pat. No. 3,871,378, issued Mar. 18, 1975 to Duncan, et al., incorporated herein by reference. Napkins made with a fibrous web of the present invention as the absorbent pad have better fluid containment properties than conventional napkins.

For use in towel sheets where wet tensile strength is important, the cellulose web must be treated with a wet strength additive. Conventional wet strength additives like melamine formaldehyde, urea formaldehyde or a latex are suitable for use herein. Such wet strength additives however, have a lower hydrophilicity then cellulose and their use in absorbent webs tends to reduce the useful capacity and the wicking rate of these webs. It has now been discovered that impregnating the web with a cellulose ester and subsequently hydrolyzing the ester results in adequate bonding of the web without any loss of useful volume or wicking rates. Indeed, it has been found that use of cellulose esters in this way tends to improve the wicking rates of cellulose microfiber webs; therefore, this constitutes a preferred embodiment of this invention. Cellulose acetate is available in large quantities at low cost and is the preferred cellulose ester for use herein.

For its use as a binder in the absorbent webs of this invention, the cellulose ester is dissolved in a suitable solvent, e.g. acetone. The solution should be sufficiently concentrated to provide deposition of the cellulose ester or the fiber. Solutions of too high a concentration, however, have a high viscosity and may not fully penetrate the absorbent web. In general, concentrations in the range of from about 0.2% to about 2% by weight are preferred for this purpose.

The absorbent web is immersed in the cellulose ester solution. Complete wetting is expedited when the air pressure is reduced so that air leaves the absorbent web more readily. After soaking the web is taken out of the solution, drained, and immersed in a solution of an alkaline material. 1% solutions of strong bases, like NaOH, KOH, NaOCH$_3$ or NH$_4$OH, in methanol are suitable. The web is subsequently rinsed with water and dried.

Microfibers suitable for the absorbent webs of this invention can very conveniently be formed from thermoplastic polymers. Virtually any thermoplastic polymer is suitable for use herein, in particular the polyolefins, the polyesters, the polyamides and the polyvinyls. Suitable examples of polyolefins are polyethylene and polypropylene; an example of a polyester is poly(ethylene terephthalate); nylon 6,6 is an example of a polyamide suitable for use herein; a suitable polyvinyl is polyvinylchloride. For most reasons polyethylene, polypropylene and poly(ethylene terephthalate) are preferred.

Melt-blowing or melt-spinning of such materials can be used to produce fibers of the required thickness. In the melt-blowing process molten polymer is extruded through a spinneret and subsequently stretched by a stream of hot air. A web is formed by gravity laying of the fibers on a belt conveyor. The warm fibers form a bond when they touch, thus ensuring a high strength of web. The melt-blowing process is described in more detail in U.S. Pat. No. 3,755,527, issued Aug. 28, 1973 to Keller, et al., the disclosure of which is incorporated herein by reference.

The melt-spinning process suitable for preparing fibers found in this invention is the so-called biconstituent spinning process. A description of this process is found in B. P. Corbman, "Textiles: Fiber to Fabric", fifth edition, 1975, McGraw Hill, New York, at page 62. The principle is that two molten polymers are coextruded through a spinneret. The resulting fiber consists of thin fibers of one polymer suspended in the other polymer. Upon dissolution of the latter polymer, microdenier fibers of the former material are obtained. The microfibers can be formed into a web by air-laying or solvent laying, in the same way as described for cellulose fibers. Web strength of the web may be increased by heat fusion, whereby the web is heated to a temperature at which the fibers become soft.

The thermoplastic web is subsequently hydrophilized. This may be done by chemically modifying the surface of the fibers, or by coating the fibers with a hydrophilic material. It has been discovered that excellent results are obtained when the structure is treated with colloidal silica. Still better results are obtained when the silica treatment is followed by a treatment with a solution of a melamine-formaldehyde, a polyvinylamide, or urea-formaldehyde resin. Particularly suitable resins for use herein are the ionic water-soluble vinylamide polymers having sufficient glyoxal-reactive amide substituents and —CH—OH—CHO substituents to be thermosetting and wherein the ratio of the number of —CH—OH—CHO substituents to the number of glyoxal reactive amide substituents are in excess of 0.06:1. These resins are more fully disclosed in U.S. Pat. No. 3,556,932, issued Jan. 19, 1971 to Cescia, et al., which is incorporated herein by reference.

Typically, the web is saturated with a 0.05% to 0.2% colloidal silica solution at a pH of from about 2 to about 5 for about 1 to 30 minutes, subsequently in a 0.05% to 0.2% solution of the resin, and then dried in an oven at about 65° C. The order of treatment may be reversed, but best results are obtained when the web is first treated with silica, then with the resin.

Very good absorbent webs are also obtained when the thermoplastic microfiber webs are treated with cellulose ester and subsequently hydrolized according to the process described above.

Hydrophilized thermoplastic microfiber webs have water absorption properties which are similar or superior to the properties of the cellulose microfiber webs of this invention. Hydrophilized thermoplastic microfiber webs may therefore be used in e.g., disposable diapers, disposable napkins and towel sheets in the same way as described hereinabove for the cellulose microfiber webs. Moreover, the thermoplastic microfiber webs are free of linting. This makes such webs particularly suitable for use as surgical sponges or as lining insurgical gowns and other applications where freedom of linting is of particular importance.

DETERMINATION OF USEFUL CAPACITY

The useful absorption capacities of fibrous webs were determined by their water absorption and desorption behavior. The basic procedure and the design of the apparatus are described by Burgeni and Kapur, "Capillary Sorption Equilibria in Fiber Masses", *Textile Research Journal,* 37 (1967) 362, which publication is incorporated herein by reference.

The absorption apparatus consists of a horizontal capillary tube, approximately 120 cm long, connected by a valve to a fluid reservoir. The end of the tube is connected by tygon tubing to a glass funnel containing an ASTM 4–8 micron frit on which the absorbent web sample is placed. The glass frit funnel is mounted on a vertical pole. The height of the frit above the capillary tube determines the hydrostatic suction being exerted on the sample. In a typical absorption/desorption experiment the volume of absorbed water is determined as a function of hydrostatic suction, starting at 100 cm.

The water absorption properties of a web are not primarily determined by the absorption capacity under soaking conditions (hydrostatic pressure=0), but rather by its ability to soak up water in competition with another material such as a table top or skin (hydrostatic pressure <0). It has been found that absorption data at −25 cm H$_2$O hydrostatic pressure and of dodecane at −12 cm dodecane pressure correlate well with liquid partition tested on a hard surface and with spill wipe-up performance under representative real life conditions i.e. with the useful capacity. This useful capacity can be calculated from the absorption/desorption isotherms. Due to hysteresis the absorbed volumes at −25 cm H$_2$O are different for the absorption branch and the desorption branch. The useful capacity is defined as the mean value of the two.

A simplified test was developed to determine the useful capacity of an absorbent web. In this test, the absorbed volume at −25 cm is measured. Next, the frit containing the sample is lowered to zero hydrostatic pressure and the equilibrium value of sorbed volume measured. Then the frit is raised again to the 25 cm mark and the absorbed volume at −25 cm in the desorption mode is determined.

EXAMPLE I

Abaca fiber drylap was defiberized in a hammer mill type disintegrator, resulting in fibers of about 10 microns diameter. A web was formed by air laying of the fibers. Calendering at 30 PSI (about $20 \times 10^6$ N/m$^2$) pressure resulted in a web density of 0.06 g/cm$^3$. The web was saturated with a solution of 0.8% cellulose acetate in acetone. About 18% by weight of cellulose acetate was deposited in the web. The saturated web was drained for about 20 seconds and then transferred onto a plastic sheet in a hood to dry. After drying the web was placed in a 1% solution of NaOH in methanol for 15 minutes, then rinsed for 15 minutes in a water flow of 4.5 liters/min at about 50° C., and subsequently placed in a holding tank with water at 50° C. for about 45 minutes. The wet web was blotted with 6 mm felt and placed in a forced-air oven at 60° C. until dry (about 30–40 minutes). The fiber thickness was established by scanning electron microscopy (SEM) to be around 10 microns.

The physical properties of the abaca web were compared with a typical commercially available disposable towel sheet (BOUNTY from The Procter & Gamble Company). This commercial towel is a wet laid web of wood pulp fibers, reinforced with a water solution polyacrylamide wet strength additive (Parez 631 NC resin from American Cyanamid Company). The physical properties of the abaca web and the BOUNTY towel are compared in the table below:

| Physcial Properties Comparison | | |
|---|---|---|
| | BOUNTY | Abaca |
| Average fiber diameter (microns) | 30 | 10 |
| Density (g/cm$^3$ at 552 N/m$^2$) | 0.07 | 0.07 |
| Useful Capacity (ml/g) | 2.8 | 5.8 |
| Strength (Dry) (g/mm) | 35 | 37 |
| (Wet) (g/mm) | 8.3 | 4.1 |

The data clearly show that the useful capacity of the micro-fibrous abaca web is far superior to that of the BOUNTY towel, although the densities of the two absorbent webs (and hence their theoretical capacities) are very similar.

Other samples of abaca fiber web are treated with cellulose triacetate, cellulose formate, cellulose propionate and cellulose butyrate, and subsequently hydrolyzed in NaOH/methanol. The resulting webs have excellent water absorption and wet strength properties.

EXAMPLE II

Preparation of a glass microfiber absorbent web.

Binder preparation

In a glass 1 liter reactor 570 ml of 3% sodium methoxide in methane was made by adding 10 g of sodium to 570 ml methanol. Then, 200 g pellets of an ethylene vinyl acetate copolymer (30–40% vinyl acetate) were added. The temperature was kept at 55° C. for one hour and then raised to 65° C. (reflux) for 4 hours to complete the hydrolysis. The reactor contents was drained through a sieve to strain out the hydrolyzed pellets. After addition of 500 ml methanol 50 ml water and 20 ml acetic acid to the pellets the mixture was refluxed for 1 hour to remove remaining caustic and purify the hydrolyzed ethylene vinyl acetate. Then the liquid was drained off and the pellets were dried overnight in an oven at 50°–70° C. 40 g dried pellets were dissolved in 400 ml toluene at 110° C. Upon slow cooling to room temperature (cooling time about 1 hour) a suspension of the binder material was formed.

Preparation of absorbent structure

In an explosion-proof blender 1 part glass microfiber (1 micron) was disintegrated into 200 parts hexane. An amount of binder suspension corresponding to 0.33 parts dry weight of binder was mixed in. The blend was diluted with 300 ml hexane. The diluted mixture was poured into a Buchner funnel and allowed to drain by gravity. The remaining hexane was allowed to evaporate. After hexane and toluene odors had disappeared the web was heated in an oven at 150° C. for 10 minutes and removed from the filter paper. The web had a density of about 0.05 g/cm$^3$.

Absorption Performance

The absorption performance of the glass microfiber absorbent web was compared with that of a commercial disposable towel (BOUNTY from The Procter & Gamble Company). Methanol was the sorption fluid.

| | BOUNTY | Glass Fiber |
|---|---|---|
| Capacity on soaking | 10 ml/g | 14 ml/g |
| Useful capacity | 3 ml/g | 11 ml/g |
| Useful capacity (% of soaking cap.) | 30 | 79 |

The data show that the glass microfiber structure has a useful capacity which is a large fraction of the capacity on soaking. As a result the glass microfiber web has a useful capacity which is 3.6 times that of a conventional cellulose fiber web, although its soaking capacity is only 40% higher than that of the conventional web.

EXAMPLE III

Glass fibers of 1 micron diameter are disintegrated in hexane, using the method of Example II. A web is formed by draining the fibers on a Buchner funnel. After drying the web is soaked in a 0.8% solution of cellulose acetate in acetone. The binder is hydrolized using the method of Example I. The resulting absorbent web has a density of 0.055 g/cm$^3$, a high useful capacity and good wicking properties.

EXAMPLE IV 500 g hardwood sulfite pulp was disintegrated into microfibers in a colloid mill at 2.5% concentration for two hours. After this treatment about 80% of the fibrous material had a fiber diameter ranging from 8 to 15 microns. The fiber mixture was dried by solvent exchange into acetone and addition of excess acetic anhydride. An absorbent web was formed by solvent exchange into hexane. The binder suspension of Example II was added in an amount corresponding to 25% of the weight of the fiber. The web was drained, dried and heat-set according to the method of Example II. The resulting absorbent web had a density of 0.09 g/cm$^3$, and absorption properties far superior to those of a conventional disposable towel.

EXAMPLE V

A suspension of hardwood sulfite pulp fibers of 0.5% consistency was passed three times through a Gaulin M-3 homogenizer at $55 \times 10^6$ N/m$^2$ pressure. Samples were taken after each pass through the homogenizing valve assembly. Scanning Electron Microscopy revealed that the degree of fibrillation increases with each pass. After two passes, more than 50% of the fibrous material had a fiber diameter of less than 15 microns; the average fiber diameter after the third pass was about 5 microns, with reasonable preservation of fiber length.

Low density webs (density less than 0.15 g/cm³) were formed by freeze drying the homogenized samples. Absorption properties of these webs were compared to those of a web formed by wet-laying of non-homogenized hardwood sulfite pulp fibers. The actual capacity was determined by absorption of water or dodecane at zero pressure. The useful capacity was determined by water absorption at −25 cm.

Capillary Sorption Data

WATER

| Sample | Fiber Diameter (microns) | Density (g/cm³) | Actual Cap. (ml/g) | Useful Cap. (ml/g) |
| --- | --- | --- | --- | --- |
| Non-hom. | 30 | 0.026 | 13.6 | 5.5 |
| 2 × hom. | 12 | 0.015 | 14.7 | 7.8 |
| 3 × hom. | 5 | 0.011 | 15.2 | 8.6 |

The data show that by reducing the fiber diameter, the useful capacity of otherwise identically prepared absorbent webs is significantly increased.

EXAMPLE VI

Freeze-dried webs of non-homogenized hardwood sulfite pulp fibers and of the 2×homogenized hardwood sulfite pulp (HSP) fibers of Example V were treated with cellulose acetate binder and subsequently deacetylated according to the method described in Example I. The capillary sorption properties of these webs were compared with those of a conventional disposable towel sheet and of a solvent laid non-homogenized hardwood sulfite pulp fiber web.

The presence of the hydrolyzed cellulose acetate binder dramatically improved the collapse resistance of the structure. The fibrillization of the pulp fibers resulted in an absorbent web which was far superior to a conventional towel sheet.

EXAMPLE VII

Two polypropylene fiber webs were made using a melt blown technique described in U.S. Pat. No. 3,755,527, issued Aug. 28, 1973 to Keller et al. In this technique polypropylene pellets were fed into an extruder where they were melted. The melt was extruded through a nozzle. The polypropylene emerging from the die was contacted with high temperature, high velocity blowing air. The air flow drew the polymer to fibers of the required thickness. A secondary flow of cool air quenched the fibers to solid state. The fibers were laid on a collector screen in a continuous web. Self bonding occurred in the lay-down zone due to fiber entanglement and surface attraction of the thin fibers.

A third polypropylene fiber web was prepared by a melt spinning technique as follows. A mixture of nine parts polystyrene pellets and 1 part polypropylene pellets were dry blended to a total weight of 9 kg. This blend was compounded on a twin screw extruder and extruded at a rate of about 14 kg per hour. The spinneret diameter was about 0.8 mm, the air temperature about 230° C.; 8 g of the resulting blend fiber was mixed with 150 ml methyl ethyl butane and worked in a laboratory blender at moderate impeller speed for 2–3 minutes. The mix was filtered through a BOUNTY towel and the filtrate discarded. The fiber mass was mixed with a fresh portion of solvent and worked in the blender as described above. Six cycles were performed to assure that all the polystyrene was removed. Following the last filtration a part of the extracted polypropylene was dispersed in t-butanol another part in benzene, a structure formed using a Buchner funnel and finally air dried or freeze dried. Fiber thickness distributions were determined by SEM. The results are given below.

Fiber Diameter and Denier Comparison

| Sample Description | Diameter (microns) |
| --- | --- |
| Melt blown, Sample A | 1.3–6.0 |
| Melt blown, Sample B | 1.3–2.0 |
| Blend Extruded | 0.2–0.5 |

The webs are treated with cellulose acetate and subsequently diacetylated according to the method described in Example I. All webs have useful capacities significantly higher than conventional towel sheets.

EXAMPLE VIII

Melt blown polypropylene and polyester fiber webs were made by the method described in Example VII. The webs were hydrophilized as follows.

A melt blown fiber web was immersed in a 0.1% colloidal silica solution at pH 3.5. A vacuum of about 630 mm Hg (about $85 \times 10^3$ N/m²) was exerted on the vessel containing the fabric and solution to make sure that the web became fully saturated. The vacuum was released and the saturated web was removed from the colloidal silica solution. Next the web was placed in a 0.1% solution of Parez 631 NC (a polyacrylamide resin from American Cyanamid Co.) at pH 6.0. After 10 minutes the web was removed from the solution, drained, and dried in a forced-air oven. Treatment of the webs in this manner resulted in a 4% weight increase.

Scanning electron microscopy revealed the surface deposition to be uniform. Treated fibers have a rough surface, untreated fibers are very smooth. ESCA (Electron Spectroscopy for Chemical Analysis) confirmed the presence of a significant amount of Si on the surface of the fibers.

Untreated polypropylene and polyester fiber webs did not wick water at all. The same webs, after the above described treatment, had wicking properties similar to a conventional wet-laid wood fiber towel sheet. The useful capacities of the polymer fiber sheets were more than twice the value measured for a conventional towel sheet. Thus, the silica treatment of thermoplastic microfiber webs results in these webs having vastly superior water absorption properties when compared with a conventional wood fiber absorbent web.

EXAMPLE IX

A hardwood fiber pulp of 6% consistency was treated for 30 minutes in a Noble and Wood beater operated at a beater roll pressure of 100 lb. (about 45 kg). SEM photographs revealed that essentially all fibers had a diameter of about 12 microns or less. The fibers were formed into a web with a density of 0.10 g/cm³ by freeze drying. The web had absorption properties which were vastly superior to those of a conventional towel sheet.

Hardwood fibers treated in a beater for 30 minutes under the above conditions are mixed with untreated fibers in weight ratios of 1:1, 2:1 and 3:1. The fiber mixtures are formed into webs have a density of 0.08 g/cm³. All webs have similar actual absorption capacty. The useful capacity decreases with increasing amount of untreated fibers.

EXAMPLE X

Wood pulp cellulose is converted to cellulose xanthate as follows. A load of alkali cellulose crumb is introduced into a vessel, vacuum is applied and carbon disulfide (45% based on the weight of cellulose) is drawn in. The reaction is carried out at a temperature of 30° C. for about 1½ hrs. During the reaction the mass is agitated by a rotating blade. When the reaction is complete a sodium hydroxide solution is drawn into the vessel and high-speed agitation is applied. The amount of sodium hydroxide added is calculated to result in a final solution comprising 6cellulose xanthate and 6sodium hydroxide. The solution is filtered and subsequently ripened under vacuum for two days at 17° C. The ripened solution is forced through the holes of a 0.02 mm spinneret into a sulfuric acid spinning bath. The fibers are stretched to a diameter of 8 microns.

Subsequently the web is treated with cellulose acetate as described in Example I. The cellulose ester is hydrolyzed in a 1% solution of NaOH in methanol. The treated web has absorption properties similar to the untreated web, and drastically improved wet strength properties.

In subsequent experiments the cellulose xantham solution is replaced with cellulose acetate in acetone and with cellulose triacetate in methylchloride, respectively. The solutions are spun into air instead of into sulfuric acid. Webs made with cellulose acetate and cellulose triacetate microfibers have excellent absorption and wicking properties. These properties are substantially unchanged after treatment with cellulose formate and subsequent hydrolysis. The wet strength is substantially increased after the cellulose formiate treatment.

EXAMPLE XI

A disposable diaper utilizing an absorbent web according to this invention was prepared as follows:

A fibrillated wood fiber web with a fiber diameter of about 5 microns prepared as in Example V was calendered to a caliper of about 0.3 cm and a density of about 0.1 g/cm$^3$ as measured under a confining pressure of 0.1 PSI (about $70 \times 10^3$ N/m$^2$. The web was cut into pads of 12 in.$\times$16 in. (about $30 \times 40$ cm). The pads were enveloped in wet strength tissue paper having a basis weight of about 12 pounds per 3,000 square feet (about 20 g/m$^2$), a dry tensile strength of about 700 g/inch in the machine direction and about 300 g/inch in the cross machine direction.

The enveloped pad was glued onto a 13 in.$\times$17 in. (about 33 cm$\times$43 cm) backsheet of embossed polyethylene film having a melt index of about 3 and a density of about 0.92 g/cm$^3$. The ends of the backsheet were folded over the enveloped pad and attached with glue. Finally, the absorbent pad was covered with a topsheet of a hydrophobic but water and urine pervious material. (Webline No. F 6211 from the Kendall Co. of Walpole, Mass., comprised of a non-woven rayon bonded with an acrylic latex).

The diapers had superior water and synthetic urine absorption, wicking and containment characteristics. In the same way, diapers are made using for the absorbent pad abaca fiber webs prepared as in Example I and silica treated polyester microfiber webs prepared as in Example IX. The diapers have superior water and urine absorption properties as compared to conventional diapers.

EXAMPLE XII

Sanitary napkins employing a fibrous web pursuant to this invention are prepared as follows:

An air-laid fibrillated wood fiber web with a fiber diameter of about 5 microns, prepared as in Example V, is calendered to a caliper of about 0.14 cm and a density of about 0.1 g/cm$^3$ as measured under a confining pressure of 0.1 PSI (about $70 \times 10^3$ N/M$^2$). The web is cut into a pad of 8 in.$\times$2 in. (about 20 cm$\times$5 cm) with tapered ends. On top of this pad is placed a second pad (rectangular) of 5 in. $\times$2 in. (about 13 cm$\times$5 cm). The combined pad structure is placed against a waterproof backing sheet (8 in. $\times$2 in., tapered) of embossed hard polyethylene having an embossed caliper of 2.3 mils. The structure is covered with a top sheet of non-woven, 3 denier needle punched polyester fabric having a density of about 0.03 g/cm$^3$ and a caliper of about 2.3 mm. The thus covered structure is placed on a 9 in. $\times$3 in. (about 23 cm$\times$7.5 cm) bottom sheet of hydrophobic, spinbonded non-woven polyester having a measured weight of about 15 g/m$^2$. The bottom sheet is prefolded upwardly by means of heat and pressure which bonds the superposed sheets together. The resulting absorbent structure is useful as a sanitary napkin and has superior properties of absorption and containment of menses exudate. Sanitary napkins with similar properties are formed using hydrophilized polyester webs, hydrophylized polypropylene and abaca microfiber webs for the absorbent pads.

EXAMPLE XIII

Surgical sponges pursuant to this invention are prepared as follows:

The silica treated polyester web of Example VIII is formed into an absorbent web of circular form with a diameter of 3 in. (about 7.5 cm), a thickness of 1 in. (about 2.5 cm) and a density of 0.08 g/cm$^3$. The pad can be used as a surgical sponge with excellent blood and lymph absorption properties. The sponge is essentially free of linting. A surgical sponge with essentially the same properties is obtained when silica coated polypropylene prepared as in Example VIII is used instead of the polyester.

EXAMPLE XIV

The silica coated polyester fiber web of Example VIII is formed into a sheet of 1 mm thickness and a density of 0.06 g/cm$_3$. The sheet material is used as lining material in a surgical gown. The lining effectively prevents perspiration fluid from dripping down the surgeon's arms.

Similarly effective linings are obtained with cellulose acetate treated polyester microfiber webs, with silica treated polypropylene webs and with cellulose acetate treated polypropylene webs.

What is claimed is:

1. A fibrous absorbent web comprising at least about 50% of hydrophilic microfibers having a diameter of from about 0.01 microns to about 15 microns, said web having a density of from about 0.01 g/cm$^3$ to about 0.15 g/cm$^3$.

2. The fibrous absorbent web of claim 1 wherein the hydrophilic microfibers have a diameter of from about 0.5 microns to about 10 microns.

3. The fibrous absorbent web of claim 1 which has a density of from about 0.04 g/cm$^3$ to about 0.10 g/cm$^3$.

4. A fibrous absorbent web consisting essentially of hydrophillic microfibers having a diameter of from about 0.5 micron to about 10 microns said web having a density of from about 0.04 g/cm$^3$ to about 0.10 g/cm$^3$.

5. The fibrous absorbent web of claim 4 wherein the hydrophilic microfibers are cellulose fibers.

6. The fibrous absorbent web of claim 5 wherein the hydrophilic microfibers are selected from the group consisting of wheat fibers, rice fibers, abaca fibers and mixtures thereof.

7. A fibrous absorbent web comprising at least about 50% of hydrophilic microfibers of a thermoplastic material, said microfibers having a diameter of from about 0.5 microns to about 10 microns, and said web having a density of from about 0.04 g/cm$^3$ to about 0.10 g/cm$^3$.

8. The fibrous absorbent web of claim 7 wherein the thermoplastic material is glass; a polyolefin; a polyester; a polyamide; or a polyvinyl.

9. The fibrous absorbent web of claim 8 wherein the thermoplastic material is polypropylene.

10. The fibrous absorbent web of claim 8 wherein the thermoplastic polymer is poly(ethylene terephtalate).

11. A process for making a fibrous absorbent web comprising the steps of
selecting a fiber mixture comprising at least about 50% of microfibers having a diameter of from about 0.01 microns to about 15 microns;
forming the fibers into a web which has a density of from about 0.01 g/cm$^3$ to about 0.15 g/cm$^3$;
immersing the web in a solution of a cellulose ester; and
hydrolyzing the cellulose ester to cellulose.

12. A process for making a fibrous absorbent web comprising the steps of
selecting a fiber mixture comprising at least about 50% of microfibers having a diameter of from about 0.01 microns to about 15 microns;
forming the fibers into a web which has a density of from about 0.01 g/cm$^3$ to about 0.15 g/cm$^3$;
immersing the web in a colloidal silica solution; and
immersing the web in a solution of a wet-strength resin selected from the group consisting of the melamine formaldehyde resins, the urea formaldehyde resins and the polyvinylamide resins.

13. A process for making a fibrous absorbent web comprising the steps of:
selecting a fiber mixture comprising at least about 50% of cellulose microfibers having a diameter of from about 0.01 microns to about 15 microns; and
forming the fibers into a web which has a density of from about 0.01 g/cm$^3$ to about 0.15 g/cm$^3$.

14. The process of claim 11 wherein the solution of the cellulose ester is a solution in acetone, and the hydrolyzing step is carried out with a solution of about 1% NaOH in methanol.

15. The process of claim 11 wherein the cellulose ester is cellulose acetate.

16. The process of claim 12 wherein the colloidal silica solution has a concentration of from about 0.05% to about 0.2% and a pH of from about 2 to about 5.

17. The process of claim 12 wherein the wet-strength resin solution has a concentration of from about 0.05% to about 0.2%.

18. The process of claim 11 wherein the fibers consist of a cellulose derivative selected from the group consisting of cellulose xanthate, cellulose acetate; cellulose triacetate; and rayon.

19. The process of claim 11 wherein the fiber mixture consists essentially of microfibers having a diameter of from about 0.5 micron to about 10 microns and wherein said fiber mixture is formed into a web having a density of from about 0.04 g/cm$^3$ to about 0.10 g/cm$^3$.

20. A disposable diaper comprising the fibrous absorbent web of claim 1.

21. A sanitary napkin comprising the fibrous absorbent web of claim 1.

22. A towel sheet comprising the fibrous absorbent web of claim 1.

23. A surgical sponge comprising the fibrous absorbent web of claim 7.

24. A surgical gown comprising the fibrous absorbent web of claim 7.

* * * * *